US010736398B2

(12) United States Patent
Fisher et al.

(10) Patent No.: US 10,736,398 B2
(45) Date of Patent: Aug. 11, 2020

(54) APPARATUS AND METHOD FOR PULLING A STRAND OF HAIR

(71) Applicant: The Procter & Gamble Company, Cincinnati, OH (US)

(72) Inventors: Brian Keith Fisher, Cincinnati, OH (US); Daniel E. Machenheimer, Union, KY (US); Richard Craig Maupin, Okeana, OH (US); William Alphonso Bennett, Cincinnati, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 295 days.

(21) Appl. No.: 15/836,377

(22) Filed: Dec. 8, 2017

(65) Prior Publication Data
US 2018/0160788 A1 Jun. 14, 2018

Related U.S. Application Data

(60) Provisional application No. 62/432,845, filed on Dec. 12, 2016.

(51) Int. Cl.
A45D 26/00 (2006.01)
A45D 44/00 (2006.01)
A61B 5/00 (2006.01)

(52) U.S. Cl.
CPC ......... A45D 26/0076 (2013.01); A45D 44/00 (2013.01); A61B 5/0048 (2013.01);
(Continued)

(58) Field of Classification Search
CPC ............ A45D 44/02; A45D 26/0076; A45D 26/0023; A45D 26/0028; A45D 26/0033;
(Continued)

(56) References Cited

U.S. PATENT DOCUMENTS 4,185,106 A 1/1980 Dittmar et al.
5,424,435 A 6/1995 Hani et al.
(Continued)

FOREIGN PATENT DOCUMENTS

CH 353846 A 4/1961
EP 0800814 A2 10/1997
(Continued)

OTHER PUBLICATIONS

All final and non-final office actions for U.S. Appl. No. 15/581,187.
(Continued)

Primary Examiner — Tan-Uyen T Ho
Assistant Examiner — Chima U Igboko
(74) Attorney, Agent, or Firm — Alexandra S. Anoff

(57) ABSTRACT

A hair pulling apparatus includes a frame having a longitudinal axis, a first leg extending from the frame, a movable leg spaced apart from the first leg, the movable leg extending from the frame and movable, linearly, relative to the frame, a control system comprising a processor to execute a plurality of pulling profile instructions stored in memory, a linear actuator operatively coupled to the control system and constructed to move linearly along the longitudinal axis relative to the frame, a gripper coupled to the linear actuator, and a load cell coupled to the linear actuator. When one or more of the plurality of pulling profile instructions stored in memory are executed by the processor, the control system causes the linear actuator to retract along the longitudinal axis, applying a pulling force to a strand of hair gripped by the gripper in order to measure the pulling force.

16 Claims, 4 Drawing Sheets

(52) U.S. Cl.
CPC ........ *A61B 5/448* (2013.01); *A45D 2044/007* (2013.01); *A61B 5/442* (2013.01)

(58) Field of Classification Search
CPC ... G01N 2033/0077; G01N 2033/0078; G01N 2033/0088; G01N 3/00; G01N 3/08; G01N 3/10; G01N 3/16; G01N 3/165; G01N 3/30; G01N 3/307; G01N 3/32; G01N 2203/00; G01N 2203/0001; G01N 2203/0003; G01N 2203/0005; G01N 2203/0007; G01N 2203/0008; G01N 2203/001; G01N 2203/0012; G01N 2203/0014; G01N 2203/0016; G01N 2203/0017; G01N 2203/003; G01N 2203/0032; G01N 2203/0033; G01N 2203/0042; G01N 2203/0044
See application file for complete search history.

(56) References Cited

U.S. PATENT DOCUMENTS

| | | | |
|---|---|---|---|
| 5,675,013 | A | 10/1997 | Hani et al. |
| 5,792,961 | A * | 8/1998 | Giebner .................. G01N 3/08 73/786 |
| 8,980,876 | B2 | 3/2015 | Schwartz et al. |
| 8,986,664 | B2 | 3/2015 | DiColandrea et al. |
| 10,543,157 | B2 | 1/2020 | Davis |
| 2010/0274261 | A1* | 10/2010 | Grieshaber ........ A45D 26/0028 606/133 |
| 2011/0060195 | A1 | 3/2011 | De Noray et al. |
| 2012/0003300 | A1 | 1/2012 | Isaacs et al. |
| 2012/0136007 | A1 | 5/2012 | Mootha et al. |
| 2013/0109664 | A1 | 5/2013 | Schwartz et al. |
| 2017/0312206 | A1 | 11/2017 | Davis |

FOREIGN PATENT DOCUMENTS

| | | |
|---|---|---|
| GB | 2207051 A | 1/1989 |
| JP | S5655857 A | 5/1981 |
| JP | S5810630 A | 1/1983 |
| JP | S58165035 A | 9/1983 |
| JP | H03152439 A | 6/1991 |
| JP | 2001172159 A | 6/2001 |
| JP | 2008007476 A | 1/2008 |
| JP | 2009096777 A | 5/2009 |
| JP | 2009137889 A | 6/2009 |
| WO | WO2011051948 A2 | 5/2011 |
| WO | WO2014027370 A1 | 2/2014 |
| WO | WO2014095289 A2 | 6/2014 |

OTHER PUBLICATIONS

Gleyzer et al, "Activation of a PGC-1-related Coactivator (PRC)-dependent Inflammatory Stress Program Linked to Apoptosis and Premature Senescence", Journal of Biological Chemistry (2013), 288 (12), 8004-8015.

Gohil et al., "Nutrient-sensitized screening for drugs that shift energy metabolism from mitochondrial respiration to glycolysis", Nature Biotechnology, vol. 28, 3, 2010 249-257.

Laura A. Wyness et al., "Trichotillometry: the reliability and practicality of hair pluckability as a method of nutritional assessment", Nutrition Journal, 2007, 6:9.

Makoto Akashi et al., "Noninvasive method for assessing the human circadian clock using hair follicle cells", PNAS, 2010, vol. 107, No. 35, 15643-15648.

PCT International Search Report and Written Opinion for PCT/US2017/030023 dated Sep. 22, 2017.

PCT International Search Report and Written Opinion for PCT/US2017/065541 dated Feb. 19, 2018.

Piérard-Franchimont et al., "Nudging hair shedding by antidandruff shampoos. A comparison of 1% ketoconazole, 1% piroctone olamine and 1% zinc pyrithione formulations", Int J Cosmet Sci. Oct. 2002;24(5):249-56.

"Some aspects of the mechanical behavior of hair" by Wj Hamburger, published in the Toilet Goods Association, No. 14, Dec. 1950.

"L'Oreal to launch new active to increase hair density", Andrew McDougall, Breaking News on Cosmetics Formulation & packaging in Europe, Jun. 21, 2012, http://www.cosmeticsdesign-europe.com/content/view/print/648430, 2 pages.

"Nudging hair shedding by antidandruff shampoos. A comparison of 1% ketoconazole, 1% piroctone olamine and 1% zinc pyrithione formulations", C. Pierard-Franchimont et al., International Journal of Cosmetic Science, 2002, 24, 249-256.

P007: Hypoxia and Human Hair Follicle Stem/Progenitor Cells, Gaianne Gentry et al, L'Oreal Research and Innovation, Clichy, France, Int J Trichology, Apr.-Jun. 2012; 4(2). Abstract.

"Skin Rejuvenation through HIF-1a Modulation", Andrea Pagani et al, Special Topic, www.PRSJournal.com, vol. 141, No. 4, 8 pages, Apr. 2018.

* cited by examiner

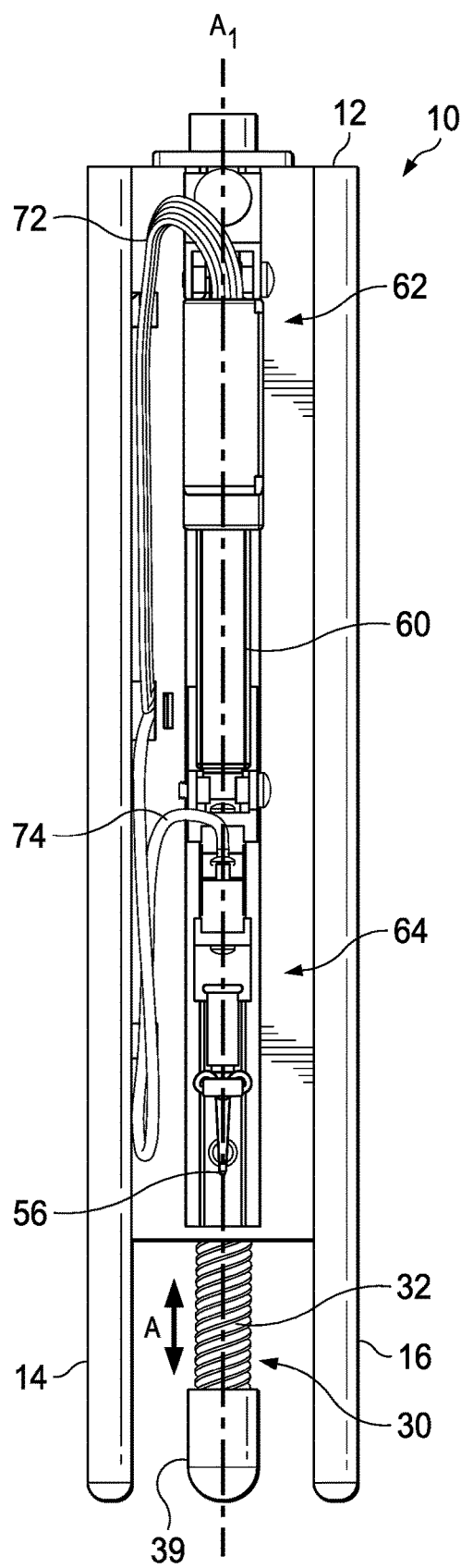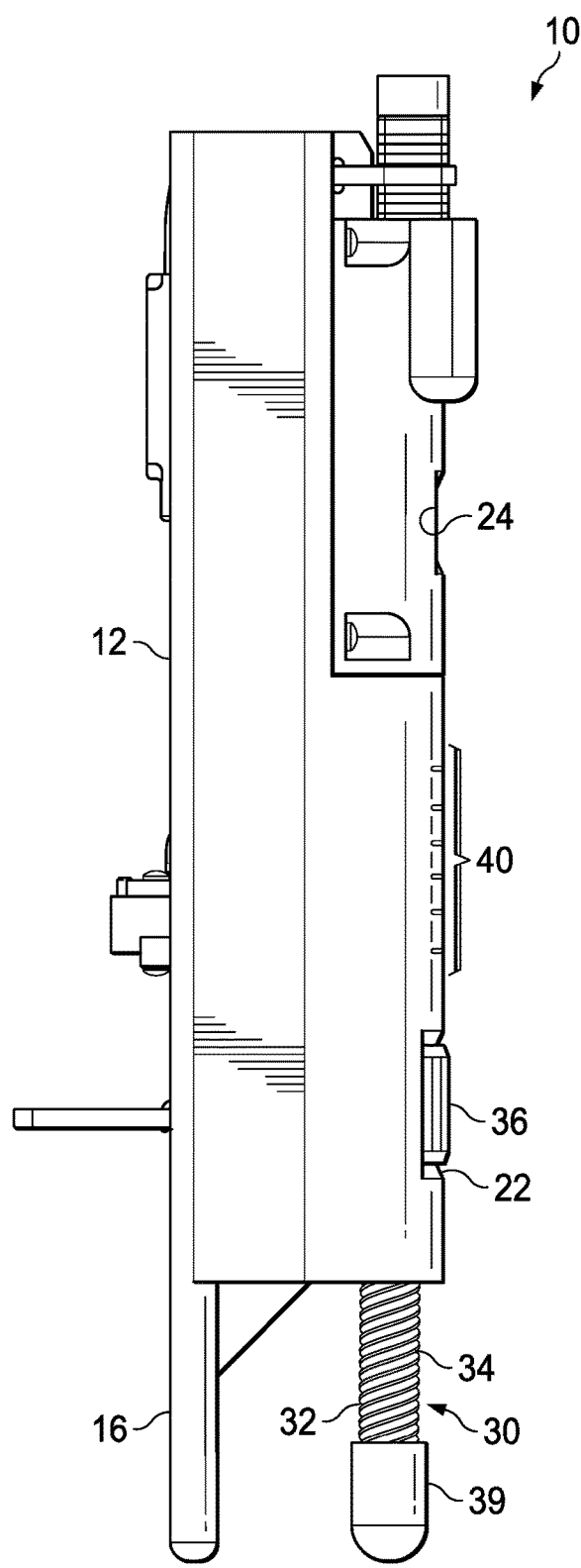
FIG. 3
FIG. 4

APPARATUS AND METHOD FOR PULLING A STRAND OF HAIR

BACKGROUND OF THE INVENTION

The consumer products industry is continually releasing a variety of new and improved consumer products. As such, the consumer products industry is continually looking for methods to improve consumer products and test such products. As such, there is a need for improved devices and methods to test consumer products, the effectiveness of such products, and/or hair and skin properties.

SUMMARY OF THE INVENTION

In one embodiment, an apparatus constructed to pull a strand of hair includes a frame having a longitudinal axis and a first end; a first leg extending from the first end of the frame; a movable leg spaced apart from the first leg, the movable leg extending from the first end of the frame and movable, linearly, relative to the frame; a control system comprising a processor to execute a plurality of pulling profile instructions stored in memory; a linear actuator operatively coupled to the control system and constructed to move linearly along the longitudinal axis relative to the frame, the linear actuator having a distal end; a load cell coupled to the linear actuator; and a gripper coupled to the distal end of the linear actuator, the gripper constructed to grip a strand of hair; wherein when one or more of the plurality of pulling profile instructions stored in memory are executed by the processor, the control system causes the linear actuator to retract along the longitudinal axis, applying a pulling force to a strand of hair gripped by the gripper; and wherein the load cell is configured to measure the pulling force.

In another embodiment, a method of testing hair or skin properties, the method includes setting a first leg and second leg of a hair plucking device upon a surface; orienting the hair plucking device relative to the surface to provide a desired pull angle; gripping, by a gripper, a strand of hair of a subject; activating a control system comprising a plurality of pulling profile instructions stored in memory, wherein upon activation of the control system, the control system executes a selected one of a plurality of pulling profile instructions, and wherein a non-selected one of the plurality of pulling profile instructions differs from the selected one of the plurality of pulling profile instructions in at least any one of the following: threshold pull force, pull distance, pull time, pull force over time, pull velocity, pull frequency, amount of time between pulls, or whether a static or constant pull force is maintained during the breaks between pulls with increasing pull force; retracting, by the control system, a linear actuator in accordance with the selected one of the plurality of pulling profile instructions to apply a pulling force to the strand of hair; and measuring, by a load cell coupled to the linear actuator, the pulling force.

In another embodiment, a method of testing hair or skin properties includes adjusting a movable leg relative to a frame of a hair plucking device; gripping, by a gripper, a strand of hair of a subject; activating a control system comprising a plurality of pulling profile instructions stored in memory, wherein upon activation of the control system, the control system executes a selected one of a plurality of pulling profile instructions, and wherein a non-selected one of the plurality of pulling profile instructions differs from the selected one of the plurality of pulling profile instructions in at least any one of the following: threshold pull force, pull distance, pull time, pull force over time, pull velocity, pull frequency, amount of time between pulls, or whether a static or constant pull force is maintained during the breaks between pulls with increasing pull force; retracting, by the control system, a linear actuator in accordance with the selected one of the plurality of pulling profile instructions to apply a pulling force to the strand of hair; and measuring, by a load cell coupled to the linear actuator, the pulling force.

BRIEF DESCRIPTION OF THE DRAWINGS

FIG. 3 is a rear view of the hair pluck device of FIG. 1;

FIG. 4 is a side elevational view of the hair pluck device of FIG. 1;

DETAILED DESCRIPTION OF THE INVENTION

Figure 1:
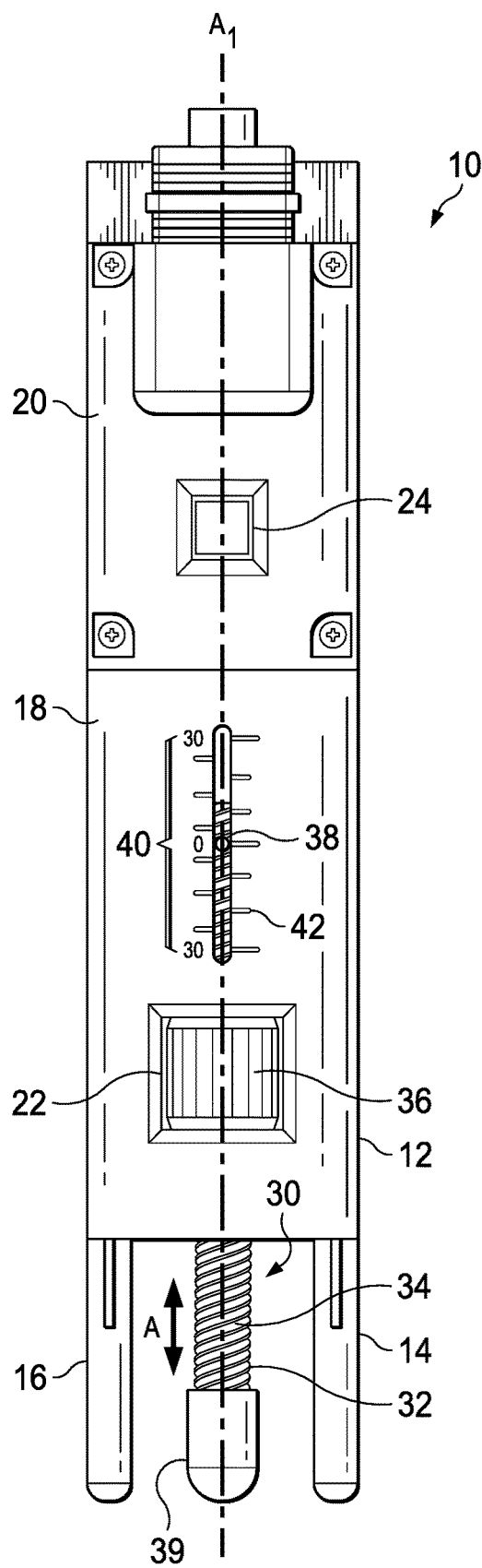
FIG. 1 is an isometric view of a hair pluck device according to one or more embodiments.
Figure 2:
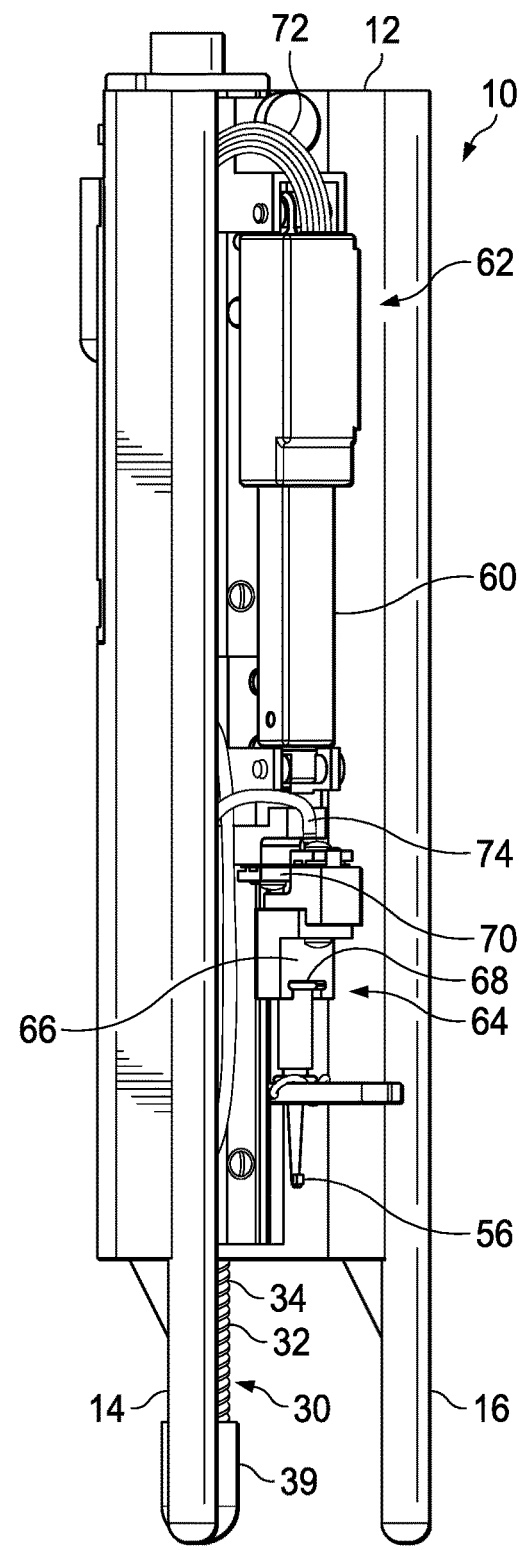
FIG. 2 is a rear isometric view of the hair pluck device of FIG. 1.

Referring to FIGS. 1-4, an embodiment of a device 10 constructed to pull and/or pluck one or more strands of hair from a subject is shown. The device 10 may be coupled to a computer and/or a network via hardwired or wireless connections. The device may measure a variety of parameters such as, for example, strain forces, stress forces, etc., and transmit such measurement data to the computer and/or network over the hardwired and/or wireless connections. The computer and/or network may store, manipulate, and/or compare the measurement data. The device 10 may generally include longitudinal axis $A_1$, a frame 12, one or more legs extending away from the frame, a control system 80, a linear actuator 60 coupled to the frame 12 and coupled to the control system, a gripper 56 coupled to the linear actuator, and a load cell 70 coupled to the linear actuator. "Couple" and "coupled", as used herein, means a physical connection or coupling and/or an operative connection or coupling (e.g., electrical connection or coupling or wireless connection or coupling).

The frame 12 may include any variety of shapes, sizes, configurations, and components. It may comprise multiple components releaseably or fixedly coupled to each other or a single, integral unit. In the embodiment shown, the frame 12 includes a substantially U-shaped configuration. The device 10 may include a first plate 18 and a second plate 20 coupled to the frame 12. The first plate 18 may include a first opening 22 disposed therein. The second plate 20 may include a second opening 24 and an aperture 26 disposed therein. The first plate 18 and/or the second plate 20 may include a leg extension indicator 40. The leg extension indicator 40 may include indicia 42 marked along the aperture 26, identifying a distance one of the legs of the device 10 has been extended or retracted as will be described more fully herein below.

In certain embodiments, the frame 12 may include a first leg 14, a second leg 16, and a third leg 30 coupled to and extending from the frame 12. The legs may be spaced-apart from each other. The first, second, and third legs 14, 16, and 30, respectively, may be integrally coupled to the frame 12, releaseably coupled to the frame 12, or some combination thereof. As shown, in this embodiment, the first, second, and third legs 14, 16, and 30, respectively, are spaced-apart approximately 60 degrees from each other about the longitudinal axis $A_1$ such that the legs form a tripod configuration.

In certain embodiments, one or more of the legs may be movable relative to the frame 12. In certain embodiments, the first leg 14, second leg 16, and/or third leg 30 may be movable relative to the frame. Referring back to the embodiment illustrated in FIGS. 1-4, the first and second legs 14 and 16, respectively, are integral to the frame 12. In this embodiment, the third leg 30 is movably coupled to the frame 12. As configured, the third leg 30 moves linearly substantially parallel to the longitudinal axis $A_1$ in two opposite directions relative to the frame 12 as indicated by arrow (A). In other words, the leg 30 may protract (extend) from the frame 12 or retract (draw in) toward the frame 12.

As shown, the third leg 30 may comprise a rod 32 having external threads 34 and an end 39 distal to the frame 12. The device 10 may also include a knob 36 rotatably coupled to the frame 12. In certain embodiments, the knob 36 may be accessible through the first opening 22. The knob 36 may include internal threads (not shown) that are configured to receive the rod 32 and engage the external threads 34 of the rod. In certain embodiments, the knob 36 may be rotated in the counterclockwise direction to protract (extend) the distal end 39 of the second leg 30 away from the frame 12 (e.g., downward) and in the clockwise direction to retract (draw in) the distal end 39 of the leg 30 toward the frame 12 (e.g., upward) or vice versa. In such embodiments, the third leg 30 has an adjustable length relative the first and second legs 14 and 16, respectively, and also relative to the frame 12. This permits the three legs to be positioned upon a curved surface such as, for example, a subject's head, and still maintain the device 10 and thus the linear actuator 60 substantially normal (e.g., perpendicular) to the surface (e.g., head, scalp, etc.) or to enable the device 10 to be positioned upon a surface (e.g., a flat surface) and orient the device relative to that surface and/or a hair follicle to obtain a desired pull angle relative to the surface and/or hair follicle. This adjustability enables the device to be oriented to pull a strand of hair at different angles relative to the surface the device is placed upon and/or the hair follicle that the strand of hair is extending from.

It should be understood that in certain embodiments, the device 10 may include any number of legs such as, for example, five (5) legs, positioned in any number of configurations such as, for example, pentagonal-shaped. In certain embodiments, the device 10 may include one fixed leg and one movable or adjustable leg. It is also understood that any number of the legs may be movably coupled to the frame 12 similar to leg 30 above or by other mechanisms and methods as conventionally known or yet-to-be developed.

As set forth above, the device 10 may include a control system 80. The control system 80 may be integrated into and positioned within the frame 12 or remote from the frame 12. In the embodiment shown in the FIGS. 1-4, a conventional signal and data cable 72 may connect the control system 80 to the linear actuator 60. It should be understood that any variety of wired and/or wireless connections as set forth herein and/or conventionally known may be used to connect the control system 80 to the linear actuator 60. The control system 80 may be embodied as any type of computing device or server or capable of processing, communicating, storing, maintaining, and transferring data. For example, the control system 80 may be embodied as a server, a microcomputer, a minicomputer, a mainframe, a desktop computer, a laptop computer, a mobile computing device, a handheld computer, a smart phone, a tablet computer, a personal digital assistant, a telephony device, a custom chip, an embedded processing device, linear actuator control board, or other computing device and/or suitable programmable device. In certain embodiments, the control system 80 can be embodied as a computing device integrated with other systems or subsystems. In certain embodiments, the control system 80 may include a linear actuator control board such as, for example, those commercially available from Firgelli automation.

Figure 5:
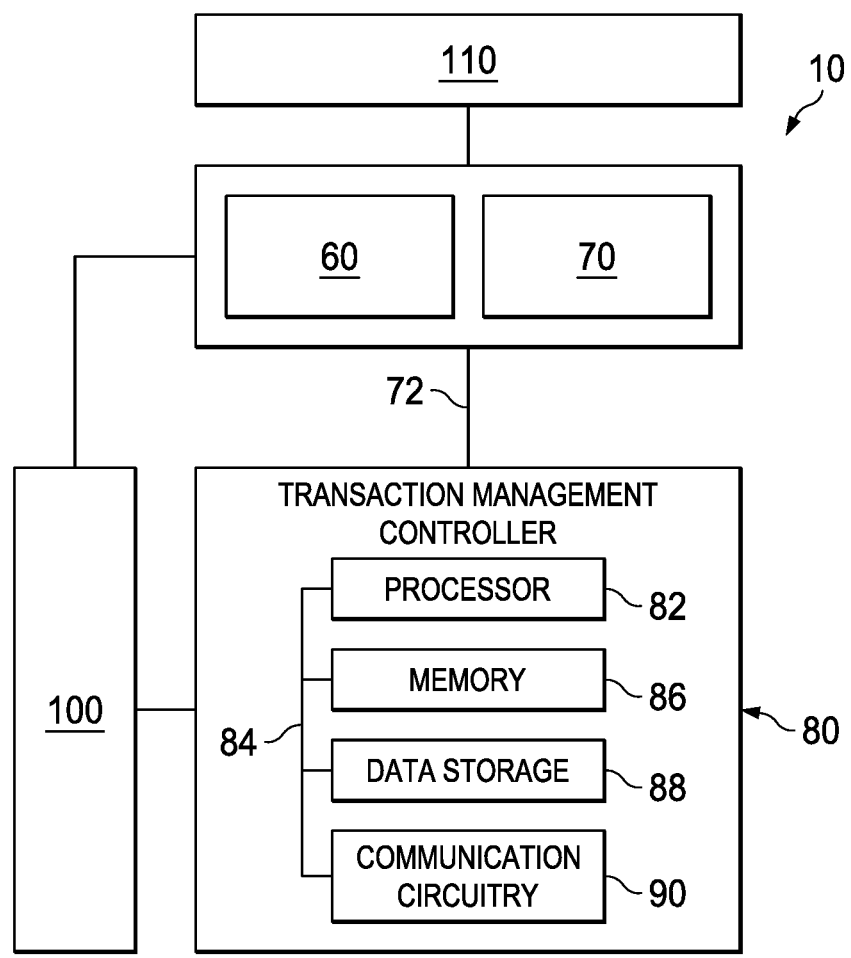
FIG. 5 is a schematic of a hair pluck device according to one or more embodiments.

In the illustrative embodiment of FIG. 5, the control system 80 may include a processor 82, a system bus 84, a memory 86, a data storage 88, and communication circuitry 90. In certain embodiments, the control system 80 may further include one or more peripheral devices. Of course, the control system 80 may include other or additional components, such as those commonly found in a server and/or computer (e.g., various input/output devices), in other embodiments. Additionally, in certain embodiments, one or more of the illustrative components may be incorporated in, or otherwise from a portion of, another component. For example, the memory 86, or portions thereof, can be incorporated in the processor 82 in some embodiments. Furthermore, it should be appreciated that the control system 80 may include other components, sub-components, and devices commonly found in a computer and/or computing device, which are not illustrated in FIG. 5 for clarity of the description. Also, it should be appreciated that any one of the illustrative components of the control system 80 set forth above may be eliminated from the system.

The processor 82 can be embodied as any type of processor capable of performing the functions described herein. For example, the processor 82 can be embodied as a single or multi-core processor, a digital signal processor, microcontroller, a general purpose central processing unit (CPU), a reduced instruction set computer (RISC) processor, a processor having a pipeline, a complex instruction set computer (CISC) processor, an application specific integrated circuit (ASIC), a programmable logic device (PLD), a field programmable gate array (FPGA), or other processor or processing/controlling circuit or controller.

In various configurations, the control system 80 includes a system bus 84 for interconnecting the various components of the control system 80. The system bus 84 may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations with the processor 82, the memory 86, and other components of the control system 80. In certain embodiments, the control system 80 may be integrated into one or more chips such as a programmable logic device or an application specific integrated circuit (ASIC). In such embodiments, the system bus 84 can form a portion of a system-on-a-chip (SoC) and be incorporated, along with the processor 82, the memory 86, and other components of the control system 80, on a single integrated circuit chip.

The memory 86 may be embodied as any type of volatile or non-volatile memory or data storage capable of performing the functions described herein. For example, the memory 86 may be embodied as read only memory (ROM), random access memory (RAM), cache memory associated with the processor 82, or other memories such as dynamic RAM (DRAM), static ram (SRAM), programmable ROM (PROM), electrically erasable PROM (EEPROM), flash memory, a removable memory card or disk, a solid state drive, and so forth. In operation, the memory 86 may store various data and software used during operation of the control system 80 such as operating systems, applications, programs, libraries, drivers, and a plurality of pulling profiles as will be described below herein.

The data storage 88 may be embodied as any type of device or devices configured for short-term or long-term storage of data such as, for example, memory devices and circuits, memory cards, hard disk drives, solid-state drives, or other data storage devices. For example, in certain embodiments, the data storage 88 includes storage media such as a storage device that can be configured to have multiple modules, such as magnetic disk drives, floppy drives, tape drives, hard drives, optical drives and media, magneto-optical drives and media, compact disc drives, Compact Disc Read Only Memory (CD-ROM), Compact Disc Recordable (CD-R), Compact Disc Rewriteable (CD-RW), a suitable type of Digital Versatile Disc (DVD) or Blu-Ray disc, and so forth. Storage media such as flash drives, solid state hard drives, redundant array of individual disks (RAID), virtual drives, networked drives and other memory means including storage media on the processor 82, or the memory 86 are also contemplated as storage devices. It should be appreciated that such memory may be internal or external with respect to operation of the disclosed embodiments. It should also be appreciated that certain portions of the processes described herein can be performed using instructions (including a plurality of pulling profiles) stored on a computer-readable medium or media that direct or otherwise instruct a computer system to perform the process steps. Non-transitory computer-readable media, as used herein, comprises all computer-readable media except for transitory, propagating signals. In certain embodiments, the data storage device 88 may be configured to store a plurality of pulling profiles of the control system 80.

The communication circuitry 90 of the control system 80 may be embodied as any type of communication circuit, device, interface, or collection thereof, capable of enabling communications between the control system 80 and the linear actuator 60 of the device 10, a remote computer 110, and/or any other computing device communicatively coupled thereto. For example, the communication circuitry 90 may be embodied as one or more network interface controllers (NICs), in certain embodiments. The communication circuitry 112 may be configured to use any one or more communication technologies (e.g., wireless or wired communications) and associated protocols (e.g., Ethernet, Wi-Fi®, WiMAX, etc.) to effect such communication.

In certain embodiments, the control system 80, remote computer 110, and/or any other computing devices can communicate with each other over one or more networks. The network(s) may be embodied as any number of various wired and/or wireless communication networks. For example, the network(s) may be embodied as or otherwise include a local area network (LAN), a wide area network (WAN), a cellular network, or a publicly-accessible, global network such as the Internet. Additionally, the network(s) may include any number of additional devices to facilitate communication between the computing devices of the system 100. In other embodiments, some or all of the control system 80 and remote computer 110 are installed and operate local to a computing device.

In one example, the control system 80 may comprise a linear actuator control board constructed to control a linear actuator. Additionally, in certain embodiments, the control system 80 may further include one or more peripheral devices. Such peripheral devices may include any type of peripheral device commonly found in a computing device such as additional data storage, memory, a hardware keyboard, a keypad, a gesture or graphical input device, a motion input device, a touchscreen interface, one or more displays, an audio unit, a voice recognition unit, a vibratory device, a computer mouse, a peripheral communication device, and any other suitable user interface, input/output device, and/or other peripheral device.

As set forth above, the memory 86 may include a plurality of pulling profiles. A pulling profile, as used herein, may include a set of instructions for execution by the processor 82 in controlling the linear actuator 60 while pulling one or more strands of hair. The pulling profile may define the magnitude of pull force, threshold pull force, pull velocity, pull distance, pull time, pull force over time, pull frequency, amount of time between pulls, whether a static or constant pull force is maintained during the breaks between pulls with increasing pull force, any combination thereof, and/or any other characteristics or properties. In certain embodiments, the memory 86 may include a plurality of pulling profiles, wherein a second one of the plurality of pulling profiles differs from a first one of the plurality of pulling profiles in at least any one of the following: threshold pull force, pull distance, pull time, pull force over time, pull velocity, pull frequency, amount of time between pulls, or whether a static or constant pull force is maintained during the breaks between pulls with increasing pull force.

In certain embodiments, the plurality of pulling profiles stored in memory of the control system 80 may include one or more of the following pulling profile instructions set forth below. In certain embodiments, the plurality of profiles stored in memory of the control system 80 may include at least any two of the pulling profile instructions set forth below.

One example of a pulling profile instruction that may be stored in memory and executed by the processor may include a pulling profile instruction to cause a gripped strand of hair to be pulled toward the frame at a constant force and speed until the gripped a strand of hair either breaks or releases from a follicle.

Another example, of a pulling profile instruction that may be stored in memory and executed by the processor may include a pulling profile instruction to cause a gripped strand of hair to be pulled toward the frame with an increasing force at a constant speed for at least a first distance ($X_1$), then hold the gripped a strand of hair under a constant pull force for a first time period ($T_1$) at that distance ($X_1$), then cause the linear actuator to repeat the previous steps n number of times or until the gripped a strand of hair either breaks or releases from a follicle.

Another example, of a pulling profile instruction that may be stored in memory and executed by the processor may include a pulling profile instruction to cause a gripped strand of hair to be pulled toward the frame with an increasing force at a constant speed for at least a first distance ($X_1$), then remove the pulling force from the gripped strand of hair for a first time period ($T_1$), then cause the linear actuator to repeat the previous steps n number of times or until the gripped a strand of hair either breaks or releases from a follicle.

Another example, of a pulling profile instruction that may be stored in memory and executed by the processor may include a pulling profile instruction to cause a gripped strand of hair to be pulled toward the frame with an increasing force at a constant speed for at least a first distance ($X_1$), then hold the gripped strand of hair under a constant pull force for a first time period ($T_1$) at that distance ($X_1$), then remove the pulling force from the strand of hair for a second time period ($T_2$), then cause the linear actuator to repeat the previous steps n number of times or until the gripped strand of hair either breaks or releases from a follicle.

Another example, of a pulling profile instruction that may be stored in memory and executed by the processor may include a pulling profile instruction to cause a gripped strand of hair to be pulled toward the frame with an increasing force at a constant speed until a predetermined pulling force is reached (e.g., a threshold pulling force), then remove the pulling force from the strand of hair for a first time period ($T_1$), then cause the linear actuator to repeat the previous steps n number of times or until the gripped strand of hair either breaks or releases from a follicle.

Another example, of a pulling profile instruction that may be stored in memory and executed by the processor may include a pulling profile instruction to cause a gripped strand of hair to be pulled toward the frame with an increasing force at a constant speed until a threshold pulling force is reached, then hold the gripped strand of hair under a constant pull force for a first time period ($T_1$) at that threshold pulling force, then remove the pulling force from the strand of hair for a second time period ($T_2$), then cause the linear actuator to repeat the previous steps n number of times or until the gripped strand of hair either breaks or releases from a follicle.

As shown, the linear actuator 60 may include a proximal end 62 and a distal end 64. In certain embodiments, the linear actuator 60 may include a clip bracket 66 coupled at the distal end 64. The clip bracket 66 may be constructed to releaseably receive and/or engage the gripper 56. In certain embodiments, the clip bracket 66 may include a receiver 68 constructed to releaseably engage an end of the gripper 56. The linear actuator 60, in certain embodiments, may be coaxially aligned with the longitudinal axis $A_1$. The linear actuator may include an electrical linear actuator such as, for example, linear actuators commercially available from Firgelli Automations, L16-P. The linear actuator may be sized in accordance with the length of stroke and force required for the desired task. The linear actuator may be powered by an AC or DC power source 80 (e.g., one or more batteries). It should be understood that other actuators may be used such as, for example, pneumatic and hydraulic actuators.

The device 10 may include a gripper 56 coupled to the distal end 64 of the linear actuator. In certain embodiments, the gripper 56 may include a flanged end 58 that is constructed to releaseably insert into and/or engage the receiver 68 of the clip bracket 66. In certain embodiments, the gripper 56 may include a micro-grabber such as, for example, a micro-grabber commercially available from DigiKey, Pamona-4233 micro-grabber. In other examples of the gripper may include, but not be limited to, alligator clips, robotic grippers, spring clips, manual vice grips, combinations thereof, etc. In certain embodiment, the gripper may be manually operated to open and close to grip and/or release one or more strands of hair. In certain other embodiments, the gripper may be coupled to the control system 80 which may send control signals to the gripper, causing it to open and close in order to grip and/or release one or more strands of hair.

As set forth above, the device may include the load cell 70 coupled to the linear actuator 60. The load cell 70 is positioned between an upper portion and a lower portion of the actuator. In such a configuration, when a strand of hair is gripped by the gripper 56 and the linear actuator 60 is caused to retract, thus placing a pulling force on the strand of hair, the opposed forces (i.e., the force created by the retracting linear actuator and the opposite force created by the strand of hair connected within the follicle) create a strain within the load cell that is measured. In certain embodiments, the load cell 70 may include a strain gauge such as, for example, LCL-005, commercially available by Omega®. In this example, the load cell has an excitation of 5 Vdc, 12V max., rated output of 2 mV/V+/−20%, zero balance of 0.3 mV/V, combined error of 0.25% FS, operating temperature of −54 to 93° C. (−65 to 200° F.), compensated temperature of −7 to 49° C. (20 to 120° F.), temperature effects of (zero balance of 0.02% FS/° F. and output of 0.02%/° F.), resistance (input and output) of 1200+/−300Ω, insulation resistance of 1000Ω@50 Vdc, seal of urethane coated, safe overload of 150% FS, full scale deflection of 0.25 to 1.27 mm (0.010 to 0.050 in.), lead wire of 9 in. shielded PVC 4-conductor 30AWG, and material of >816 gf (2 lb): 301 SS; 816 gf (2 lb) beryllium copper.

The load cell 70 may be coupled to a remote computer 110 and/or the control system 80. The remote computer 110 may include one or more networks (e.g., LAN, WAN, Internet, etc.) such that the load cell 70 may send strain and/or force data measured by it to the remote computer 110, control system 80, and/or other networks to store, manipulate, analyze, compare, transfer to other computers or networks, and/or the like. The remote computer 110 may include any and/or all of the components that the control system 80 may include and perform the same or similar functions as set forth above. The load cell 70 may be connected to the remote computer 110, the control system 80, and/or other networks (e.g., a WAN, Internet, etc.) via wired (e.g., signal and/or data cable 74) or wireless connections such as, those set forth above and/or conventionally known. In certain embodiments, the load cell 70 and/or the device 10 are coupled to the remote computer 110 via a USB wired connection. In such an embodiment, the device 10 may further include a strain gauge to USB converter coupled between the load cell 70 and the USB wired connection.

The load cell 70, control system 80, remote computer 110, and/or other sensors coupled to the device may be configured to measure, calculate, and/or store a variety of pulling data. Pulling data may include, but not be limited to, pulling force (e.g., strain), pulling force over-time (e.g., strain over-time), pulling velocity (e.g., velocity of the linear actuator), pulling time, and/or other similar measurement data. Pulling time may include, but not be limited to the period of time from the point in time wherein the linear actuator begins pulling a strand of hair to the point in time that either the linear actuator stops pulling the strand of hair or the strand of hair releases from its follicle. Pulling time may also include the cumulative amount of time for multiple pulls with such as, defined in one or more of the pulling profile instructions set forth herein. In certain embodiments, the pulling time may be calculated manually, macros, or via software by dividing the pulling velocity by the total distance traveled. In certain embodiments, the velocity may be measured via a sensor coupled to the device and/or control system 80. In certain embodiments, the device 10 may measure the pulling force every 10 ms and the distance traveled by the linear actuator. From this data, software on the control system 80 may calculate pull velocity (mm/ms). In certain embodiments, the device 10 may include a potentiometer to determine pulling velocity. The information from the potentiometer is conditioned and/or translated into the data used by the control system to determine and/or calculate velocity.

The power source 100 may be coupled to the device 10 and/or the control system 80 to provide power to any of the individual components and/or the device as a whole. The power source 100 may be an A/C and/or DC. The A/C source may be a conventional 120 volt A/C outlet. The DC source may include one or more batteries.

Figure 6:
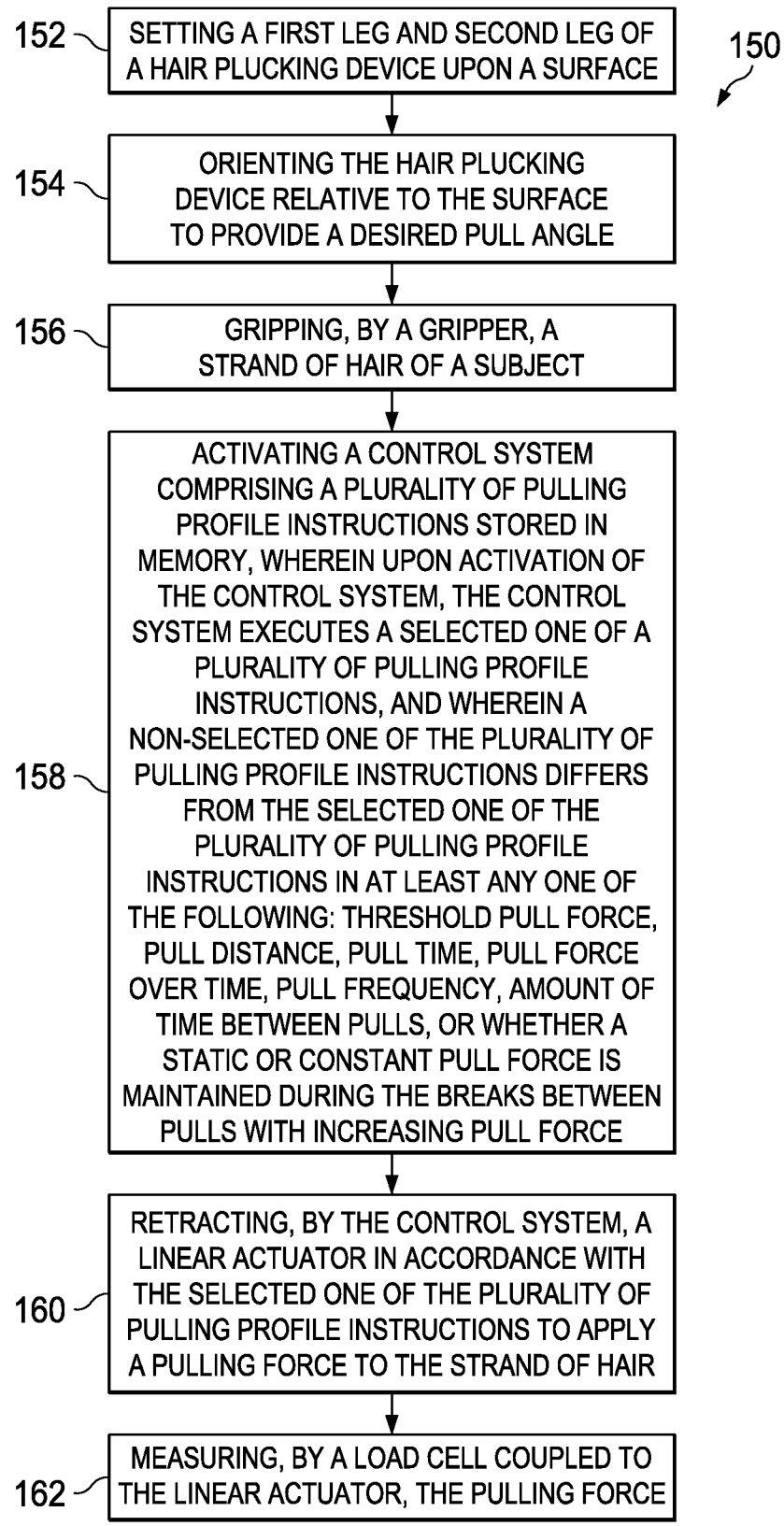
FIG. 6 is a schematic of a method of testing a hair or skin properties according to one or more embodiments.

The device 10 may be used in a variety of ways and methods in a variety of environments, including, but not limited to in a laboratory, testing facility, at home, in a retail store, and/or other locations. Referring to FIG. 6, one example of a method that the device 10 may be used in includes a method of testing hair or skin properties. In this example, the method includes setting a first leg and second leg of a hair plucking device upon a surface; orienting the hair plucking device relative to the surface to provide a desired pull angle; gripping, by a gripper, a strand of hair of a subject; activating a control system comprising a plurality of pulling profile instructions stored in memory, wherein upon activation of the control system, the control system executes a selected one of a plurality of pulling profile instructions, and wherein a non-selected one of the plurality of pulling profile instructions differs from the selected one of the plurality of pulling profile instructions in at least any one of the following: threshold pull force, pull distance, pull time, pull force over time, threshold pull force, pull distance, pull velocity, pull frequency, amount of time between pulls, or whether a static or constant pull force is maintained during the breaks between pulls with increasing pull force, pull frequency, amount of time between pulls, or whether a static or constant pull force is maintained during the breaks between pulls with increasing pull force; retracting, by the control system, a linear actuator in accordance with the selected one of the plurality of pulling profile instructions to apply a pulling force to the strand of hair; and measuring, by a load cell coupled to the linear actuator, the pulling force.

In certain embodiments of this method, the plurality of pulling profile instructions may include at least two of the following pulling profile instructions: a first pulling profile instruction to cause a gripped strand of hair to be pulled toward the frame at a constant force and speed until the gripped a strand of hair either breaks or releases from a follicle; a second pulling profile instruction to cause a gripped strand of hair to be pulled toward the frame with an increasing force at a constant speed for at least a first distance (X1), then hold the gripped a strand of hair under a constant pull force for a first time period (T1) at that distance (X1), then cause the linear actuator to repeat the previous steps n number of times or until the gripped a strand of hair either breaks or releases from a follicle; a third pulling profile instruction to cause a gripped strand of hair to be pulled toward the frame with an increasing force at a constant speed for at least a first distance (X1), then remove the pulling force from the gripped strand of hair for a first time period (T1), then cause the linear actuator to repeat the previous steps n number of times or until the gripped a strand of hair either breaks or releases from a follicle; a fourth pulling profile instruction to cause a gripped strand of hair to be pulled toward the frame with an increasing force at a constant speed for at least a first distance (X1), then hold the gripped strand of hair under a constant pull force for a first time period (T1) at that distance (X1), then remove the pulling force from the strand of hair for a second time period (T2), then cause the linear actuator to repeat the previous steps n number of times or until the gripped strand of hair either breaks or releases from a follicle; a fifth pulling profile instruction to cause a gripped strand of hair to be pulled toward the frame with an increasing force at a constant speed until a predetermined pulling force is reached (e.g., a threshold pulling force), then remove the pulling force from the strand of hair for a first time period (T1), then cause the linear actuator to repeat the previous steps n number of times or until the gripped strand of hair either breaks or releases from a follicle; or a sixth pulling profile instruction to cause a gripped strand of hair to be pulled toward the frame with an increasing force at a constant speed until a threshold pulling force is reached, then hold the gripped strand of hair under a constant pull force for a first time period (T1) at that threshold pulling force, then remove the pulling force from the strand of hair for a second time period (T2), then cause the linear actuator to repeat the previous steps n number of times or until the gripped strand of hair either breaks or releases from a follicle.

In certain embodiments, the step of orienting the hair plucking device to provide the desired pull angle may include adjusting the length of at least one of the first and second legs. In certain embodiments, the method may include communicating wirelessly between the control system and the linear actuator. In certain embodiments, the method may further include orienting a hair plucking device relative to a surface to provide a desired pull angle of a strand of hair of the subject post application of a consumer product to the subjects hair or scalp; gripping, by a gripper, the strand of hair of the subject; activating a control system, wherein upon activation of the control system, the control system executes another selected one of a plurality of pulling profile instruction stored in memory, wherein a non-selected one of the plurality of pulling profile instructions differs from the another selected one of the plurality of pulling profile instructions in at least any one of the following: threshold pull force, pull distance, pull time, pull force over time, pull velocity, pull frequency, amount of time between pulls, or whether a static or constant pull force is maintained during the breaks between pulls with increasing pull force; retracting, by the control system, a linear actuator in accordance with the another selected one of the plurality of pulling profile instructions to apply a pulling force to the strand of hair; measuring, by a load cell coupled to the linear actuator, the pulling force; and comparing the measured pulling force applied to the strand of hair prior to application of the consumer product to hair of scalp of a subject to the pulling force applied to the strand of hair post application of the consumer product to hair or scalp of the subject. It should be understood that although the examples and/or methods disclosed herein describe a strand of hair of a subject, each step and/or method may be repeated multiple times for several strands of hair from a single subject and/or may be repeated multiple times to pull a single strand of hair from each of multiple subjects or several strands of hair from each of multiple subjects.

In certain embodiments, the method may further include compiling pulling data for one or more strands of hair prior to application of a consumer product to the one or more strands of hair or a scalp of one or more subjects. In certain embodiments, the method may further include compiling pulling data for one or more strands of hair post application of the consumer product to the one or more strands of hair or the scalp of the one or more subjects. In certain embodiments, the method may further include supporting a product claim for the consumer product with this compiled data.

In certain embodiments, the device 10 may be used at a retail store or point of sale to perform a hair pluck test, demonstration, and/or one or more of the methods shown and described herein.

Examples

1. An apparatus constructed to pull a strand of hair, the apparatus comprising:

a frame having a longitudinal axis and a first end;
a first leg extending from the first end of the frame;
a movable leg spaced apart from the first leg, the movable leg extending from the first end of the frame and movable, linearly, relative to the frame;
a control system comprising a processor to execute a plurality of pulling profile instructions stored in memory;
a linear actuator operatively coupled to the control system and constructed to move linearly along the longitudinal axis relative to the frame, the linear actuator having a distal end; a load cell coupled to the linear actuator; and
a gripper coupled to the distal end of the linear actuator, the gripper constructed to grip a strand of hair;
wherein when one or more of the plurality of pulling profile instructions stored in memory are executed by the processor, the control system causes the linear actuator to retract along the longitudinal axis, applying a pulling force to a strand of hair gripped by the gripper; and
wherein the load cell is configured to measure the pulling force.

2. The apparatus according to example 1, further comprising a third leg spaced-apart from the first and second legs and extending from the first end of the frame.

3. The apparatus according to example 2, wherein the third leg is movable linearly relative to the frame.

4. The apparatus according to any one of examples 2 or 3, wherein the frame comprises an internally-threaded receiver and wherein the second leg is an externally-threaded rod that threadably engages the internally-threaded receiver.

5. The apparatus according to any of the examples 1-4, further comprising a plurality of legs spaced apart from each other and the first and second legs, each one of the plurality of legs extends from the first end of the frame.

6. The apparatus according to any one of the examples 2-5, wherein each of the first, second, and third legs comprises a respective distal end, and wherein each of the respective distal ends of the first, second, and third legs further comprises a foot releaseably coupled to each respective distal end.

7. The apparatus according to any one of the examples 2-6, wherein each of the first, second, and third legs comprises a respective distal end, and wherein each distal end of the first, second, and third legs further comprises a resilient material for gripping.

8. The apparatus according to any one of the examples 1-7, further comprising a power source coupled to the linear actuator, wherein the power source is selected from the group consisting of the following: electric, hydraulic, and pneumatic.

9. The apparatus according to any one of the examples 1-8, wherein the load cell is a strain gauge.

10. The apparatus according to any one of the examples 1-9, wherein the plurality of pulling profile instructions stored in memory include a first pulling profile instruction and a second pulling profile instruction, wherein the second pulling profile instruction differs from the first pulling profile instruction in at least any one of the following: threshold pull force, pull distance, pull time, pull force over time, pull velocity, pull frequency, amount of time between pulls, or whether a static or constant pull force is maintained during the breaks between pulls with increasing pull force.

11. The apparatus according to any one of the examples 1-10, wherein the plurality of pulling profile instructions includes at least two of the following pulling profile instructions:
a first pulling profile instruction to cause a gripped strand of hair to be pulled toward the frame at a constant force and speed until the gripped a strand of hair either breaks or releases from a follicle;
a second pulling profile instruction to cause a gripped strand of hair to be pulled toward the frame with an increasing force at a constant speed for at least a first distance ($X_1$), then hold the gripped a strand of hair under a constant pull force for a first time period ($T_1$) at that distance ($X_1$), then cause the linear actuator to repeat the previous steps n number of times or until the gripped a strand of hair either breaks or releases from a follicle;
a third pulling profile instruction to cause a gripped strand of hair to be pulled toward the frame with an increasing force at a constant speed for at least a first distance ($X_1$), then remove the pulling force from the gripped strand of hair for a first time period ($T_1$), then cause the linear actuator to repeat the previous steps n number of times or until the gripped a strand of hair either breaks or releases from a follicle;
a fourth pulling profile instruction to cause a gripped strand of hair to be pulled toward the frame with an increasing force at a constant speed for at least a first distance ($X_1$), then hold the gripped strand of hair under a constant pull force for a first time period ($T_1$) at that distance ($X_1$), then remove the pulling force from the strand of hair for a second time period ($T_2$), then cause the linear actuator to repeat the previous steps n number of times or until the gripped strand of hair either breaks or releases from a follicle;
a fifth pulling profile instruction to cause a gripped strand of hair to be pulled toward the frame with an increasing force at a constant speed until a predetermined pulling force is reached (e.g., a threshold pulling force), then remove the pulling force from the strand of hair for a first time period ($T_1$), then cause the linear actuator to repeat the previous steps n number of times or until the gripped strand of hair either breaks or releases from a follicle; or
a sixth pulling profile instruction to cause a gripped strand of hair to be pulled toward the frame with an increasing force at a constant speed until a threshold pulling force is reached, then hold the gripped strand of hair under a constant pull force for a first time period ($T_1$) at that threshold pulling force, then remove the pulling force from the strand of hair for a second time period ($T_2$), then cause the linear actuator to repeat the previous steps n number of times or until the gripped strand of hair either breaks or releases from a follicle.

12. A method of testing hair or skin properties, the method comprising:
setting a first leg and second leg of a hair plucking device upon a surface;
orienting the hair plucking device relative to the surface to provide a desired pull angle;
gripping, by a gripper, a strand of hair of a subject;
activating a control system comprising a plurality of pulling profile instructions stored in memory, wherein upon activation of the control system, the control system executes a selected one of a plurality of pulling profile instructions, and wherein a non-selected one of the plurality of pulling profile instructions differs from the selected one of the plurality of pulling profile instructions in at least any one of the following: threshold pull force, pull distance, pull time, pull force over time, pull velocity, pull frequency, amount of time between pulls, or whether a static or constant pull force is maintained during the breaks between pulls with increasing pull force;

retracting, by the control system, a linear actuator in accordance with the selected one of the plurality of pulling profile instructions to apply a pulling force to the strand of hair; and measuring, by a load cell coupled to the linear actuator, the pulling force.

13. The method according to example 12, wherein the plurality of pulling profile instructions includes at least two of the following pulling profile instructions:

a first pulling profile instruction to cause a gripped strand of hair to be pulled toward the frame at a constant force and speed until the gripped a strand of hair either breaks or releases from a follicle;

a second pulling profile instruction to cause a gripped strand of hair to be pulled toward the frame with an increasing force at a constant speed for at least a first distance ($X_1$), then hold the gripped a strand of hair under a constant pull force for a first time period ($T_1$) at that distance ($X_1$), then cause the linear actuator to repeat the previous steps n number of times or until the gripped a strand of hair either breaks or releases from a follicle;

a third pulling profile instruction to cause a gripped strand of hair to be pulled toward the frame with an increasing force at a constant speed for at least a first distance ($X_1$), then remove the pulling force from the gripped strand of hair for a first time period ($T_1$), then cause the linear actuator to repeat the previous steps n number of times or until the gripped a strand of hair either breaks or releases from a follicle;

a fourth pulling profile instruction to cause a gripped strand of hair to be pulled toward the frame with an increasing force at a constant speed for at least a first distance ($X_1$), then hold the gripped strand of hair under a constant pull force for a first time period ($T_1$) at that distance ($X_1$), then remove the pulling force from the strand of hair for a second time period ($T_2$), then cause the linear actuator to repeat the previous steps n number of times or until the gripped strand of hair either breaks or releases from a follicle;

a fifth pulling profile instruction to cause a gripped strand of hair to be pulled toward the frame with an increasing force at a constant speed until a predetermined pulling force is reached (e.g., a threshold pulling force), then remove the pulling force from the strand of hair for a first time period ($T_1$), then cause the linear actuator to repeat the previous steps n number of times or until the gripped strand of hair either breaks or releases from a follicle; or a sixth pulling profile instruction to cause a gripped strand of hair to be pulled toward the frame with an increasing force at a constant speed until a threshold pulling force is reached, then hold the gripped strand of hair under a constant pull force for a first time period ($T_1$) at that threshold pulling force, then remove the pulling force from the strand of hair for a second time period ($T_2$), then cause the linear actuator to repeat the previous steps n number of times or until the gripped strand of hair either breaks or releases from a follicle.

14. The method according to any one of the examples 12 or 13, wherein the orienting the hair plucking device to provide the desired pull angle comprises adjusting the length of at least one of the first and second legs.

15. The method according to any one of the examples 12-14, wherein the hair pluck device further comprises a third leg spaced-apart from the first and second legs and extending from the frame.

16. The method according to any one of the examples 12-15, further comprising communicating wirelessly between the control system and the linear actuator.

17. The method according to any one of the examples 12-15, further comprising:

orienting a hair plucking device relative to a surface to provide a desired pull angle of a strand of hair of the subject post application of a consumer product to the subject's hair or scalp;

gripping, by a gripper, the strand of hair of the subject;

activating a control system, wherein upon activation of the control system, the control system executes another selected one of a plurality of pulling profile instructions stored in memory, wherein a non-selected one of the plurality of pulling profile instructions differs from the another selected one of the plurality of pulling profile instructions in at least any one of the following: threshold pull force, pull distance, pull time, pull force over time, pull velocity, pull frequency, amount of time between pulls, or whether a static or constant pull force is maintained during the breaks between pulls with increasing pull force;

retracting, by the control system, a linear actuator in accordance with the another selected one of the plurality of pulling profile instructions to apply a pulling force to the strand of hair; and measuring, by a load cell coupled to the linear actuator, the pulling force.

18. The method according to example 17, further comprising comparing the measured pulling force applied to a strand of hair over a period of time prior to application of the consumer product to the pulling force applied to a strand of hair over a period of time post application of the consumer product.

19. The method according to any one of the examples 17 or 18, further comprising compiling pulling data a strand of hair prior to application of a consumer product to hair or scalp of a subject; compiling pulling data for a strand of hair post application of the consumer product to the hair or scalp of the subject; and supporting a product claim for the consumer product with this compiled data.

20. A method of testing hair or skin properties, the method comprising:

adjusting a movable leg relative to a frame of a hair plucking device;

gripping, by a gripper, a strand of hair of a subject;

activating a control system comprising a plurality of pulling profile instructions stored in memory, wherein upon activation of the control system, the control system executes a selected one of a plurality of pulling profile instructions, and wherein a non-selected one of the plurality of pulling profile instructions differs from the selected one of the plurality of pulling profile instructions in at least any one of the following: threshold pull force, pull distance, pull time, pull force over time, pull velocity, pull frequency, amount of time between pulls, or whether a static or constant pull force is maintained during the breaks between pulls with increasing pull force;

retracting, by the control system, a linear actuator in accordance with the selected one of the plurality of pulling profile instructions to apply a pulling force to the strand of hair; and measuring, by a load cell coupled to the linear actuator, the pulling force.

It should be understood that any feature and/or element of any one of the embodiments and/or examples shown and described above herein may be removed from the embodiment and/or example, replaced with a feature or element from another embodiment or example herein or replaced with an equivalent feature or element.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any embodiment disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications can be made. It is therefore intended to cover in the appended claims all such changes and modifications.

What is claimed is:

1. An apparatus constructed to pull a strand of hair, the apparatus comprising:
   a frame having a longitudinal axis and a first end;
   a first leg extending from the first end of the frame;
   a movable leg spaced apart from the first leg, the movable leg extending from the first end of the frame and movable, linearly, relative to the frame;
   a control system comprising a processor to execute a plurality of pulling profile instructions stored in memory;
   a linear actuator operatively coupled to the control system and constructed to move linearly along the longitudinal axis relative to the frame, the linear actuator having a distal end;
   a load cell coupled to the linear actuator; and
   a gripper coupled to the distal end of the linear actuator, the gripper constructed to grip a strand of hair;
   wherein when one or more of the plurality of pulling profile instructions stored in memory are executed by the processor, the control system causes the linear actuator to retract along the longitudinal axis, applying a pulling force to a strand of hair gripped by the gripper; and
   wherein the load cell is configured to measure the pulling force.

2. The apparatus of claim 1, further comprising a third leg spaced-apart from the first and movable legs and extending from the first end of the frame.

3. The apparatus of claim 2, wherein the third leg is movable linearly relative to the frame.

4. The apparatus of claim 2, wherein the frame comprises an internally-threaded receiver and wherein the movable leg is an externally-threaded rod that threadably engages the internally-threaded receiver.

5. The apparatus of claim 1, wherein the load cell is a strain gauge.

6. The apparatus of claim 1, wherein the plurality of pulling profile instructions stored in memory include a first pulling profile instruction and a second pulling profile instruction, wherein the second pulling profile instruction differs from the first pulling profile instruction in at least any one of the following: threshold pull force, pull distance, pull time, pull force over time, pull velocity, pull frequency, amount of time between pulls, or whether a static or constant pull force is maintained during the breaks between pulls with increasing pull force.

7. The apparatus of claim 1, wherein the plurality of pulling profile instructions includes at least two of the following pulling profile instructions:
   a first pulling profile instruction to cause a gripped strand of hair to be pulled toward the frame at a constant force and speed until the gripped a strand of hair either breaks or releases from a follicle;
   a second pulling profile instruction to cause a gripped strand of hair to be pulled toward the frame with an increasing force at a constant speed for at least a first distance ($X_1$), then hold the gripped a strand of hair under a constant pull force for a first time period ($T_1$) at that distance ($X_1$), then cause the linear actuator to repeat the previous steps n number of times or until the gripped a strand of hair either breaks or releases from a follicle;
   a third pulling profile instruction to cause a gripped strand of hair to be pulled toward the frame with an increasing force at a constant speed for at least a first distance ($X_1$), then remove the pulling force from the gripped strand of hair for a first time period ($T_1$), then cause the linear actuator to repeat the previous steps n number of times or until the gripped a strand of hair either breaks or releases from a follicle;
   a fourth pulling profile instruction to cause a gripped strand of hair to be pulled toward the frame with an increasing force at a constant speed for at least a first distance ($X_1$), then hold the gripped strand of hair under a constant pull force for a first time period ($T_1$) at that distance ($X_1$), then remove the pulling force from the strand of hair for a second time period ($T_2$), then cause the linear actuator to repeat the previous steps n number of times or until the gripped strand of hair either breaks or releases from a follicle;
   a fifth pulling profile instruction to cause a gripped strand of hair to be pulled toward the frame with an increasing force at a constant speed until a predetermined pulling force is reached (e.g., a threshold pulling force), then remove the pulling force from the strand of hair for a first time period ($T_1$), then cause the linear actuator to repeat the previous steps n number of times or until the gripped strand of hair either breaks or releases from a follicle; or
   a sixth pulling profile instruction to cause a gripped strand of hair to be pulled toward the frame with an increasing force at a constant speed until a threshold pulling force is reached, then hold the gripped strand of hair under a constant pull force for a first time period ($T_1$) at that threshold pulling force, then remove the pulling force from the strand of hair for a second time period ($T_2$), then cause the linear actuator to repeat the previous steps n number of times or until the gripped strand of hair either breaks or releases from a follicle.

8. A method of testing hair or skin properties, the method comprising:
setting a first leg and second leg of a hair plucking device upon a surface;
orienting the hair plucking device relative to the surface to provide a desired pull angle;
gripping, by a gripper, a strand of hair of a subject; and
activating a control system comprising a plurality of pulling profile instructions stored in memory, wherein upon activation of the control system, the control system executes a selected one of a plurality of pulling profile instructions, and wherein a non-selected one of the plurality of pulling profile instructions differs from the selected one of the plurality of pulling profile instructions in at least any one of the following: threshold pull force, pull distance, pull time, pull force over time, pull velocity, pull frequency, amount of time between pulls, or whether a static or constant pull force is maintained during the breaks between pulls with increasing pull force;
retracting, by the control system, a linear actuator in accordance with the selected one of the plurality of pulling profile instructions to apply a pulling force to the strand of hair; and
measuring, by a load cell coupled to the linear actuator, the pulling force.

9. The method of claim 8, wherein the plurality of pulling profile instructions includes at least two of the following pulling profile instructions:
a first pulling profile instruction to cause a gripped strand of hair to be pulled toward the frame at a constant force and speed until the gripped a strand of hair either breaks or releases from a follicle;
a second pulling profile instruction to cause a gripped strand of hair to be pulled toward the frame with an increasing force at a constant speed for at least a first distance ($X_1$), then hold the gripped a strand of hair under a constant pull force for a first time period ($T_1$) at that distance ($X_1$), then cause the linear actuator to repeat the previous steps n number of times or until the gripped a strand of hair either breaks or releases from a follicle;
a third pulling profile instruction to cause a gripped strand of hair to be pulled toward the frame with an increasing force at a constant speed for at least a first distance ($X_1$), then remove the pulling force from the gripped strand of hair for a first time period ($T_1$), then cause the linear actuator to repeat the previous steps n number of times or until the gripped a strand of hair either breaks or releases from a follicle;
a fourth pulling profile instruction to cause a gripped strand of hair to be pulled toward the frame with an increasing force at a constant speed for at least a first distance ($X_1$), then hold the gripped strand of hair under a constant pull force for a first time period ($T_1$) at that distance ($X_1$), then remove the pulling force from the strand of hair for a second time period ($T_2$), then cause the linear actuator to repeat the previous steps n number of times or until the gripped strand of hair either breaks or releases from a follicle;
a fifth pulling profile instruction to cause a gripped strand of hair to be pulled toward the frame with an increasing force at a constant speed until a predetermined pulling force is reached (e.g., a threshold pulling force), then remove the pulling force from the strand of hair for a first time period ($T_1$), then cause the linear actuator to repeat the previous steps n number of times or until the gripped strand of hair either breaks or releases from a follicle; or
a sixth pulling profile instruction to cause a gripped strand of hair to be pulled toward the frame with an increasing force at a constant speed until a threshold pulling force is reached, then hold the gripped strand of hair under a constant pull force for a first time period ($T_1$) at that threshold pulling force, then remove the pulling force from the strand of hair for a second time period ($T_2$), then cause the linear actuator to repeat the previous steps n number of times or until the gripped strand of hair either breaks or releases from a follicle.

10. The method of claim 8, wherein the orienting the hair plucking device to provide the desired pull angle comprises adjusting the length of at least one of the first and second legs.

11. The method of claim 10, wherein the hair pluck device further comprises a third leg spaced-apart from the first and second legs and extending from the frame.

12. The method of claim 8, further comprising communicating wirelessly between the control system and the linear actuator.

13. The method of claim 8, further comprising:
orienting a hair plucking device relative to a surface to provide a desired pull angle of a strand of hair of the subject post application of a consumer product to the subject's hair or scalp;
gripping, by a gripper, the strand of hair of the subject;
activating a control system, wherein upon activation of the control system, the control system executes another selected one of a plurality of pulling profile instruction stored in memory, wherein a non-selected one of the plurality of pulling profile instructions differs from the another selected one of the plurality of pulling profile instructions in at least any one of the following: threshold pull force, pull distance, pull time, pull force over time, pull velocity, pull frequency, amount of time between pulls, or whether a static or constant pull force is maintained during the breaks between pulls with increasing pull force;
retracting, by the control system, a linear actuator in accordance with the another selected one of the plurality of pulling profile instructions to apply a pulling force to the strand of hair; and
measuring, by a load cell coupled to the linear actuator, the pulling force.

14. The method of claim 13, further comprising comparing the measured pulling force applied to a strand of hair over a period of time prior to application of the consumer product to the pulling force applied to a strand of hair over a period of time post application of the consumer product.

15. The method of claim 13, further comprising compiling pulling data for a strand of hair prior to application of a consumer product to hair or scalp of a subject; compiling pulling data for a strand of hair post application of the consumer product to hair or the scalp of the subject; and supporting a product claim for the consumer product with this compiled data.

16. A method of testing hair or skin properties, the method comprising:
adjusting a movable leg relative to a frame of a hair plucking device;
gripping, by a gripper, a strand of hair of a subject;
activating a control system comprising a plurality of pulling profile instructions stored in memory, wherein upon activation of the control system, the control system executes a selected one of a plurality of pulling profile instructions, and wherein a non-selected one of the plurality of pulling profile instructions differs from the selected one of the plurality of pulling profile instructions in at least any one of the following: threshold pull force, pull distance, pull time, pull force over time, pull velocity, pull frequency, amount of time between pulls, or whether a static or constant pull force is maintained during the breaks between pulls with increasing pull force;

retracting, by the control system, a linear actuator in accordance with the selected one of the plurality of pulling profile instructions to apply a pulling force to the strand of hair; and measuring, by a load cell coupled to the linear actuator, the pulling force.

\* \* \* \* \*